(12) United States Patent
Lin et al.

(10) Patent No.: US 12,079,389 B2
(45) Date of Patent: Sep. 3, 2024

(54) VIBRATING DEVICE AND OPERATION METHOD THEREOF

(71) Applicant: HTC Corporation, Taoyuan (TW)

(72) Inventors: Lun-Kang Lin, Taoyuan (TW); I-Han Tai, Taoyuan (TW)

(73) Assignee: HTC Corporation, Taoyuan (TW)

( * ) Notice: Subject to any disclaimer, the term of this patent is extended or adjusted under 35 U.S.C. 154(b) by 93 days.

(21) Appl. No.: 18/161,094

(22) Filed: Jan. 30, 2023

(65) Prior Publication Data

US 2024/0256041 A1 Aug. 1, 2024

(51) Int. Cl.

| G06F 3/01 | (2006.01) |
|---|---|
| A61B 5/296 | (2021.01) |
| G01N 29/46 | (2006.01) |

(52) U.S. Cl.
CPC .............. *G06F 3/015* (2013.01); *A61B 5/296* (2021.01); *G01N 29/46* (2013.01)

(58) Field of Classification Search
None
See application file for complete search history.

(56) References Cited

U.S. PATENT DOCUMENTS

| 2018/0122197 A1* | 5/2018 | Wu | G06V 20/40 |
|---|---|---|---|
| 2018/0232051 A1* | 8/2018 | Wu | G06V 40/23 |
| 2020/0364588 A1* | 11/2020 | Knox | G06V 40/20 |
| 2022/0113799 A1* | 4/2022 | Schorey | G06F 3/015 |
| 2023/0050411 A1* | 2/2023 | Herr | A61F 2/68 |
| 2023/0266824 A1* | 8/2023 | Schorey | G06F 3/012 |
| | | | 345/156 |
| 2023/0390087 A1* | 12/2023 | Herr | A61B 5/4528 |
| 2024/0115143 A1* | 4/2024 | Thüring et al. | A61B 5/4848 |

FOREIGN PATENT DOCUMENTS

| CN | 113468635 A | * 10/2021 |
|---|---|---|
| TW | M565021 | 8/2018 |

OTHER PUBLICATIONS

"Office Action of Taiwan Counterpart Application", issued on Jun. 6, 2023, p. 1-p. 7.

* cited by examiner

*Primary Examiner* — Fekadeselassie Girma
(74) *Attorney, Agent, or Firm* — JCIPRNET

(57) ABSTRACT

A vibrating device and an operation method thereof. The vibrating device includes multiple electromyography sensors, a force sensor, multiple vibrators and a controller. The electromyography sensors are respectively disposed at different positions of a user to obtain multiple pieces of electromyography information respectively. The vibrators are disposed adjacent to or overlapping with the electromyography sensors. During a setting period, the controller makes the vibrators vibrate according to a preset vibration waveform. During the setting period, the controller records multiple pieces of force information generated by the force sensor corresponding to multiple different applied forces of the user and the pieces of electromyography information generated by the electromyography sensors. The controller obtains multiple characteristic frequency parameters according to the corresponding pieces of electromyography information. The controller establishes a relational model between the characteristic frequency parameters and the pieces of force information.

12 Claims, 4 Drawing Sheets

VIBRATING DEVICE AND OPERATION METHOD THEREOF

BACKGROUND

Technical Field

The disclosure relates to a vibrating device and an operation method thereof, and in particular to a vibrating device capable of providing a user with the most suitable vibration experience in response to various states of muscles and an operation method thereof.

Description of Related Art

The general vibrating device mostly vibrates through a fixed frequency preset by the user. Regardless of whether the user's muscles are in a tense or relaxed state, the vibrator gives the same vibration experience. Therefore, a situation where the vibration experience is not good often occurs. In the conventional technical field, the vibrator is usually set to have a fixed vibration frequency. Under such condition, when the degree of the user's muscle tension is different, the experience of the vibration feedback obtained is also different, and the degree of experience is reduced.

SUMMARY

In view of this, the disclosure provides a vibrating device and an operation method thereof, which may effectively improve a user's vibration experience.

The vibrating device of the disclosure includes multiple electromyography sensors, a force sensor, multiple vibrators and a controller. The electromyography (EMG) sensors are respectively disposed at different positions of a user to obtain multiple pieces of electromyography information respectively. The vibrators are disposed adjacent to or overlapping with the electromyography sensors. The controller is coupled to the electromyography sensors, the force sensor and the vibrators. During a setting period, the controller makes the vibrators vibrate according to a preset vibration waveform. During the setting period, the controller records multiple pieces of force information generated by the force sensor corresponding to multiple different applied forces of the user and the pieces of electromyography information generated by the electromyography sensors. The controller obtains multiple characteristic frequency parameters according to the corresponding pieces of electromyography information. The controller establishes a relational model between the characteristic frequency parameters and the pieces of force information.

The operation method of the disclosure is adapted for a vibrating device. The operation method includes: multiple pieces of electromyography information are obtained from multiple electromyography sensors respectively disposed at different positions of a user; multiple vibrators are made to vibrate during a setting period according to a preset vibration waveform; during the setting period, multiple pieces of force information generated by a force sensor corresponding to multiple different applied forces of the user and the pieces of electromyography information generated by the electromyography sensors are recorded; multiple characteristic frequency parameters are obtained according to the corresponding pieces of electromyography information; and a relational model between the characteristic frequency parameters and the pieces of force information is established.

Based on the above, the vibrating device of the disclosure obtains the pieces of electromyography information of the user through the electromyography sensors disposed at different positions of the user, and generates, through the force sensor, the pieces of force information generated corresponding to the different applied forces of the user. Next, the vibrating device may establish a relational model through the pieces of electromyography information and the pieces of force information. In this way, the vibrating device may respectively detect the degree of muscle tension and the applied force of the user through the electromyography sensors and the force sensor, and then generate the corresponding vibration intensity according to the detected results through the relational model, so as to provide the user with the most suitable vibration experience in real time.

DESCRIPTION OF THE EMBODIMENTS

Figure 1:
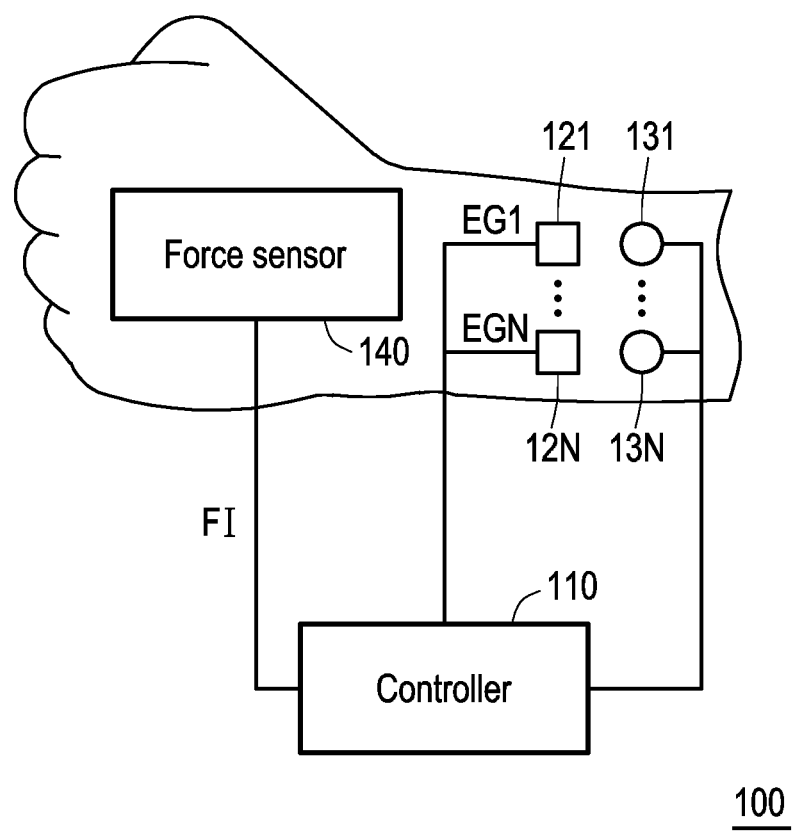
FIG. 1 is a schematic diagram of a vibrating device according to an embodiment of the disclosure.

Some embodiments of the disclosure accompanied with drawings are described in detail as follows. The reference numerals used in the following description are regarded as the same or similar elements when the same reference numerals appear in different drawings. These embodiments are only a part of the disclosure, and do not disclose all the possible implementations of the disclosure. To be more precise, the embodiments are only examples in the scope of the claims of the disclosure.

FIG. 1 is a schematic diagram of a vibrating device according to an embodiment of the disclosure. Please refer to FIG. 1. A vibrating device 100 includes a controller 110, multiple electromyography sensors 121-121N, multiple vibrators 131-13N and a force sensor 140. The controller 110 is coupled to the electromyography sensors 121-12N, the vibrators 131-13N and the force sensor 140. The electromyography sensors 121-12N are respectively disposed at different positions of a user, so the electromyography sensors 121-12N may obtain multiple pieces of electromyography information EG1-EGN respectively. The vibrators 131-13N may be disposed adjacent to the electromyography sensors 121-12N respectively, or may be disposed overlapping with the electromyography sensors 121-12N respectively.

During a setting period, the vibrating device 100 may perform a customized setting action corresponding to the user. During the setting period, the controller 110 may make the vibrators 131-13N vibrate according to a preset vibration waveform. In addition, during the setting period, the controller 110 may further simultaneously record multiple pieces of force information FI generated by the force sensor 140 corresponding to multiple different applied forces of the user, and record the pieces of electromyography information EG1-EGN correspondingly generated by the electromyography sensors 121-12N.

In an embodiment, the electromyography sensors 121-12N may be disposed at different positions of the user's arm. The electromyography sensors 121-12N may respectively detect the degree of muscle tension at the locations therein, so as to obtain the pieces of electromyography information EG1-EGN respectively. At the same time, the user may touch the force sensor 140 (for example, hold the force sensor 140). At the same time, for example, the user may gradually increase the strength of holding the force sensor 140 over time. Correspondingly, the force sensor 140 may generate multiple pieces of force information FI corresponding to multiple different applied forces exerted by the user during multiple time intervals in the setting period. During the setting period, the controller 110 may also correspondingly record the pieces of electromyography information EG1-EGN generated by the electromyography sensors 121-12N and the pieces of force information FI generated by the force sensor 140 in the above-mentioned time intervals. In this way, the controller 110 may obtain the corresponding relationship between the degree of muscle tension at multiple positions on the user's arm and the force exerted by the user's hand.

Next, the controller 110 may obtain multiple characteristic frequency parameters according to the corresponding pieces of electromyography information. Specifically, the controller 110 may respectively perform a conversion from the time domain to the frequency domain through the pieces of electromyography information EG1-EGN in the time domain, and obtain the characteristic frequency parameters corresponding to the pieces of electromyography information EG1-EGN respectively. In detail, the controller 110 may perform the conversion from the time domain to the frequency domain by executing the Fourier transform (FT), and further obtain the characteristic frequency parameters.

Figure 2:
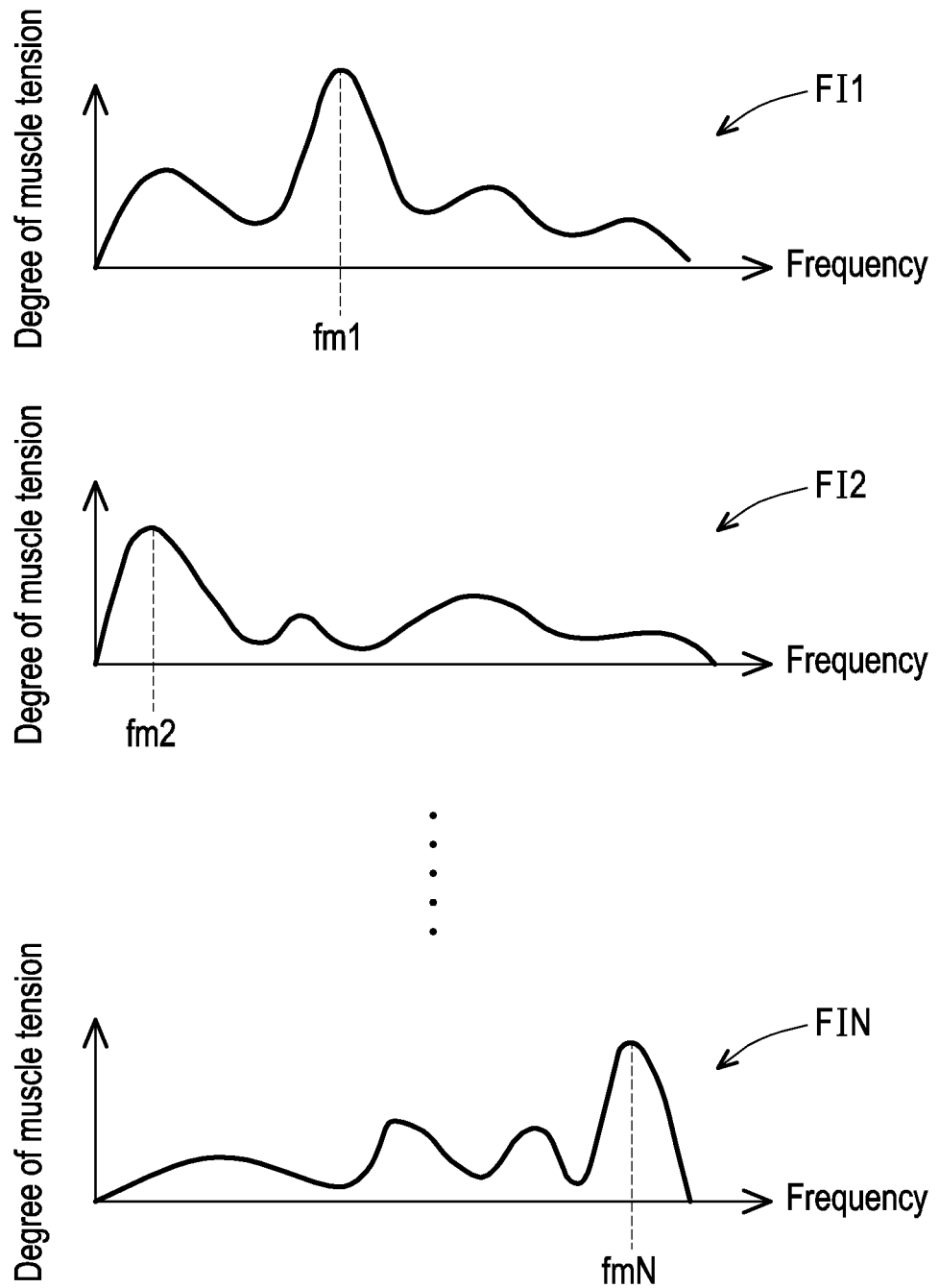
FIG. 2 is a schematic diagram of a calculation method of the characteristic frequency parameter of electromyography information according to an embodiment of the disclosure.

To further illustrate, the controller 110 may record multiple time points in the setting period for each of the pieces of electromyography information EG1-EGN, and obtain timing information of the pieces of electromyography information respectively. Next, the controller 110 may perform the Fourier transform on the timing information of each of the pieces of electromyography information EG1-EGN, and obtain frequency domain information of each of the pieces of electromyography information EG1-EGN. Please refer to FIG. 1 and FIG. 2 simultaneously. FIG. 2 is a schematic diagram of a calculation method of the characteristic frequency parameter of electromyography information according to an embodiment of the disclosure. The controller 110 may perform the Fourier transform on the timing information of each of the pieces of electromyography information EG1-EGN, and obtain pieces of frequency domain information FI1-FIN of each of the pieces of electromyography information EG1-EGN. Furthermore, the pieces of frequency domain information FI1-FIN of each of the pieces of electromyography information EG1-EGN may be analyzed, and characteristic frequency parameters fm1-fmN corresponding to the pieces of frequency domain information FI1-FIN with the maximum degree of muscle tension may be obtained.

Further, the controller 110 may establish a relational model between the characteristic frequency parameters fm1-fmN and the pieces of force information FI, and complete the setting action of the relational model during the setting period. Specifically, the controller 110 may establish the relational model between the characteristic frequency parameters fm1-fmN and the pieces of force information FI through machine learning or neural network learning for the force information FI and the corresponding characteristic frequency parameters fm1-fmN. In an embodiment, the neural network may be a convolutional neural network (CNN), a recurrent neural network (RNN), or a deep neural network (DNN), which is not limited by the disclosure.

After completing the setting action in the setting period, the vibrating device 100 may enter an application period. During the application period, the controller 110 may adjust the vibration intensity of each of the vibrators 131-13N according to the relational model established in the setting period. Specifically, during the application period, the electromyography sensors 121-12N may detect the degrees of muscle tension at different positions of the user, so as to obtain the pieces of electromyography information EG1-EGN. The force sensor 140 may detect the forces exerted by the user to obtain the pieces of force information FI. The controller 110 inputs the pieces of electromyography information EG1-EGN and the pieces of force information FI into the relational model in real time, so as to obtain a spectral gain parameter corresponding to each of the electromyography sensors 121-12N. Further, the controller 110 may respectively adjust the vibrators 131-13N adjacent to or overlapping with the corresponding electromyography sensors 121-12N according to the spectral gain parameters. For example, the controller 110 may adjust the vibration intensity of the vibrator 131 according to the spectral gain parameter corresponding to the electromyography sensor 121. In this way, the vibrators 131-13N may provide the most suitable vibration intensity for the user according to the degree of the user's muscle tension in real time, which may effectively improve the user's vibration experience.

In terms of the hardware structure, the controller 110 may be a processor with computing capability. Alternatively, the controller 110 may be designed through a hardware description language (HDL) or any other digital circuit design method known to those skilled in the art, and a hardware circuit implemented through a field programmable gate array (FPGA), a complex programmable logic device (CPLD), or an application-specific integrated circuit (ASIC). The vibrators 131-13N may be any type of vibrator known to those skilled in the art, and there is no specific limit. The force sensor 140 may be a capacitive force sensor, a multi-axis force sensor, or a strain gauge force sensor, which is not limited by the disclosure.

Figure 3:
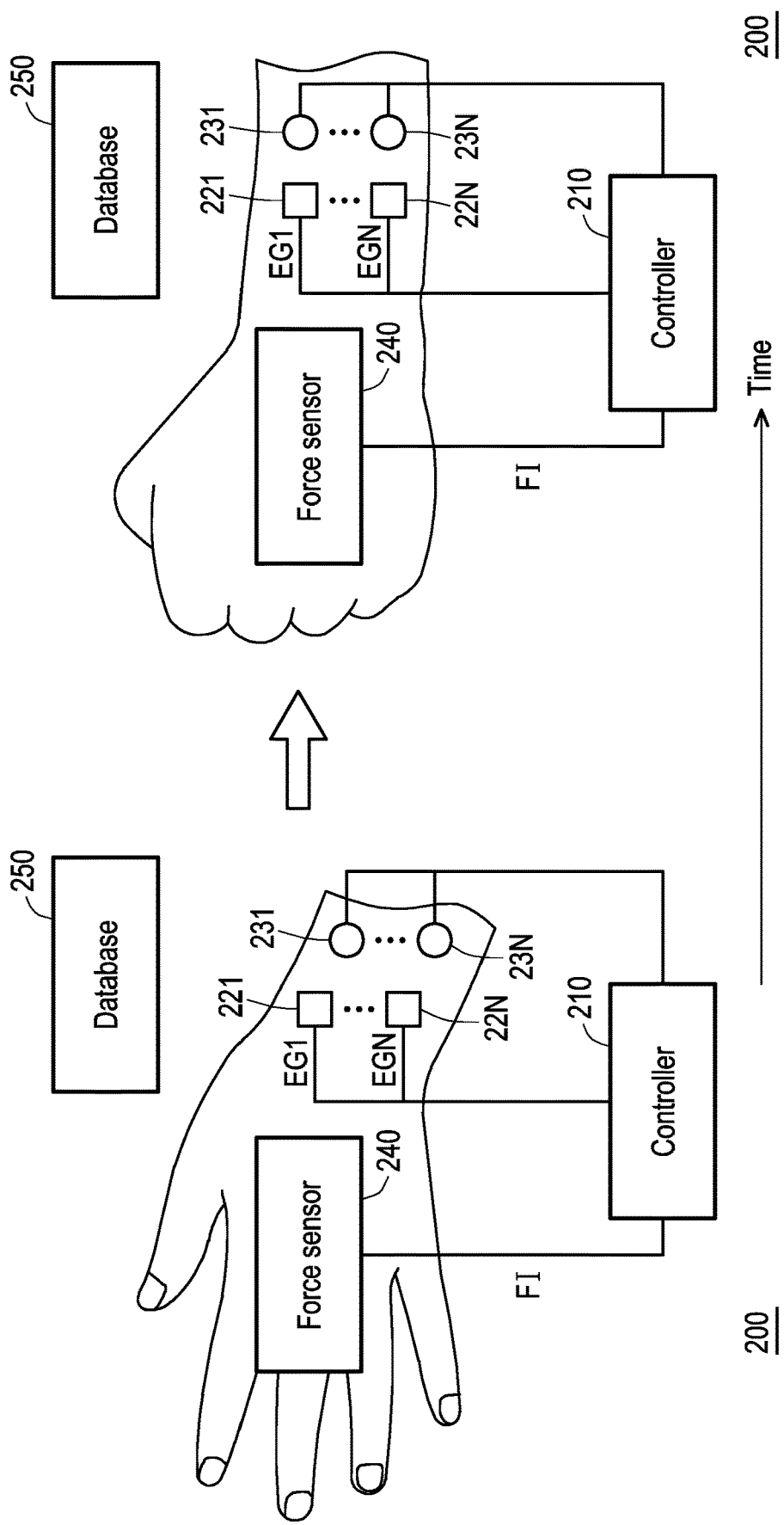
FIG. 3 is a schematic action diagram of the setting operation of the vibrating device in the setting period according to an embodiment of the disclosure.

FIG. 3 is a schematic action diagram of the setting operation of the vibrating device in the setting period according to an embodiment of the disclosure. Please refer to FIG. 3. In the embodiment, a vibrating device 200 includes a controller 210, multiple electromyography sensors 221-22N, multiple vibrators 231-23N, a force sensor 240 and a database 250. The database 250 stores multiple pieces of vibration information corresponding to the vibrators 231-23N. In an embodiment, during the setting period, the controller 210 may make the user increase the quantity value of each applied force in time sequence, and the controller 210 simultaneously records the pieces of electromyography information EG1-EGN to obtain the timing information of the pieces of electromyography information EG1-EGN. For example, during the setting period, the controller 210 makes the user's hand gradually increase the applied force from the fully relaxed state to the fully clenched state over time. Of course, in other embodiments of the disclosure, the controller 210 may also make the user's hand gradually reduce the applied force from the fully clenched state to the fully relaxed state over time, or make the user's hand repeatedly clenched and relaxed without fixed limits.

At the same time, the controller 210 records the pieces of force information FI generated by the force sensor 240 corresponding to the user's incrementally applied force in time sequence and the pieces of electromyography information EG1-EGN generated by the electromyography sensors 221-22N. Next, the controller 210 may obtain multiple characteristic frequency parameters according to the corresponding pieces of electromyography information EG1-EGN. Further, the controller 210 establishes a relational model between the characteristic frequency parameters and the force information FI. In this way, during the application period, the controller 210 may adjust the vibration intensity of the vibrators 231-23N according to the relational model, which may effectively improve the user's vibration experience.

The details of the actions of the controller 210 during the setting period have been described in detail in the foregoing embodiment, and the descriptions are not repeated here.

Figure 4:
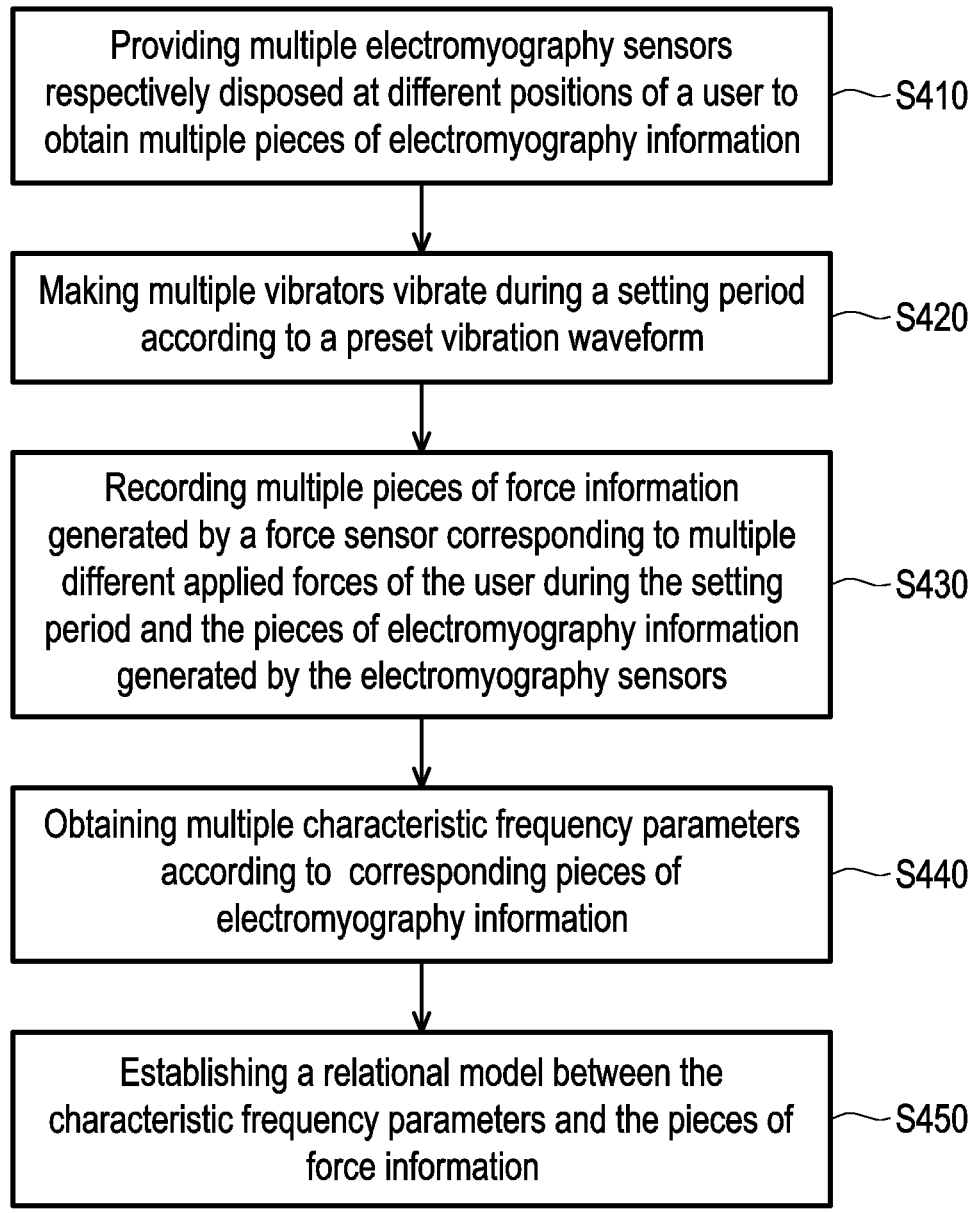
FIG. 4 is a flowchart of an operation method adapted for a vibrating device according to an embodiment of the disclosure.

FIG. 4 is a flowchart of an operation method adapted for a vibrating device according to an embodiment of the disclosure. The operation method of the embodiment may be implemented by the vibrating device 100 in FIG. 1. Please refer to FIG. 1 and FIG. 4. Firstly, in step S410, the pieces of electromyography information EG1-EGN are respectively obtained by the electromyography sensors 121-12N respectively disposed at different positions of the user. In step S420, the vibrators 131-13N vibrate during the setting period according to a preset vibration waveform. In addition, in step S430, during the setting period, the pieces of force information FI generated by the force sensor 140 corresponding to multiple different applied forces of the user and the pieces of electromyography information EG1-EGN generated by the electromyography sensors 121-12N are recorded. Next, in step S440, multiple characteristic frequency parameters are obtained according to the corresponding pieces of electromyography information EG1-EGN. Finally, in step S450, a relational model between the characteristic frequency parameters and the pieces of force information FI is established. The implementation details of step S410-step S450 have been described in detail in the above-mentioned embodiment, so the descriptions are not repeated here.

To sum up, the vibrating device of the disclosure establishes a relational model between the characteristic frequency parameters and the pieces of force information in advance during the setting period. In this way, during the application period, the vibrating device may respectively detect the degree of muscle tension and the applied force of the user through the electromyography sensors and the force sensor, and then generate the corresponding vibration intensity according to the detected results through the relational model. In this way, the vibrating device of the disclosure may effectively improve the user's vibration experience.

What is claimed is:

1. A vibrating device, comprising:
a plurality of electromyography sensors, respectively disposed at different positions of a user to obtain a plurality of pieces of electromyography information respectively;
a force sensor;
a plurality of vibrators, disposed adjacent to the electromyography sensors; and
a controller, coupled to the electromyography sensors, the force sensor and the vibrators, and configured for:
making the vibrators vibrate during a setting period according to a preset vibration waveform;
recording a plurality of pieces of force information generated by the force sensor corresponding to a plurality of different applied forces of the user during the setting period and the pieces of electromyography information generated by the electromyography sensors;
obtaining a plurality of characteristic frequency parameters according to the pieces of electromyography information corresponding to thereof; and
establishing a relational model between the characteristic frequency parameters and the pieces of force information.

2. The vibrating device according to claim 1, further comprising:
a database, configured for storing a plurality of pieces of vibration information corresponding to the vibrators.

3. The vibrating device according to claim 1, wherein the controller further comprises:
making the user increase a quantity value of each of the applied forces in time sequence.

4. The vibrating device according to claim 1, wherein the controller obtains the characteristic frequency parameters through Fourier transform calculation.

5. The vibrating device according to claim 1, wherein the controller establishes the relational model through machine learning or neural network learning.

6. The vibrating device according to claim 1, wherein the controller further comprises:
adjusting a vibration intensity of each of the vibrators according to the relational model during an application period.

7. An operation method adapted for a vibrating device, comprising:
obtaining a plurality of pieces of electromyography information respectively from a plurality of electromyography sensors respectively disposed at different positions of a user;
making a plurality of vibrators vibrate during a setting period according to a preset vibration waveform;
recording a plurality of pieces of force information generated by a force sensor corresponding to a plurality of different applied forces of the user during the setting period and the pieces of electromyography information generated by the electromyography sensors;
obtaining a plurality of characteristic frequency parameters according to the pieces of electromyography information corresponding to thereof; and
establishing a relational model between the characteristic frequency parameters and the pieces of force information.

8. The operation method according to claim 7, further comprising:
providing a database to store a plurality of pieces of vibration information corresponding to the vibrators.

9. The operation method according to claim 7, further comprising:
making the user increase a quantity value of each of the applied forces in time sequence.

10. The operation method according to claim 7, further comprising:
obtaining the characteristic frequency parameters through Fourier transform calculation.

11. The operation method according to claim 7, further comprising:
establishing the relational model through machine learning or neural network learning.

12. The operation method according to claim 7, further comprising:
   adjusting a vibration intensity of each of the vibrators according to the relational model during an application period.

* * * * *